(12) United States Patent
Agunbiade (10) Patent No.: US 12,106,843 B1
(45) Date of Patent: Oct. 1, 2024

(54) DIGITAL PLATFORM, SYSTEM, AND METHOD FOR PROVIDING THIRD-PARTIES/USERS MEAL PLANS PROVIDED BY PROFESSIONAL DIETICIANS VIA A DIGITAL HEALTH AND FITNESS PLATFORM

(71) Applicant: Bolaji Agunbiade, North York (CA)

(72) Inventor: Bolaji Agunbiade, North York (CA)

( * ) Notice: Subject to any disclaimer, the term of this patent is extended or adjusted under 35 U.S.C. 154(b) by 0 days.

(21) Appl. No.: 18/502,020

(22) Filed: Nov. 5, 2023

(51) Int. Cl.
*G16H 20/60* (2018.01)
*G06Q 10/08* (2024.01)
*G16H 10/60* (2018.01)

(52) U.S. Cl.
CPC .............. *G16H 20/60* (2018.01); *G06Q 10/08* (2013.01); *G16H 10/60* (2018.01)

(58) Field of Classification Search
None
See application file for complete search history.

(56) References Cited

U.S. PATENT DOCUMENTS

2022/0392610 A1* 12/2022 Kiani .................... G16H 20/30

FOREIGN PATENT DOCUMENTS

KR 2021094206 A * 7/2021
WO WO-2020107097 A1 * 6/2020 ........... A61B 5/0077

* cited by examiner

Primary Examiner — Kristy A Haupt (57) ABSTRACT

The invention relates to a system, method and a digital platform revolutionizing health and wellness management through personalized meal planning and fitness tracking. This user-centric system collects vital personal data, encompassing body metrics, fitness goals, dietary preferences, and allergies, through an intuitive interface. Utilizing sophisticated algorithms, including Basal Metabolic Rate (BMR), Resting Metabolic Rate (RMR), and Total Daily Energy Expenditure (TDEE), the platform precisely calculates tailored dietary requirements for each user. A robust data repository empowers registered dietitians, nutritionists, and professionals to upload meal offerings, categorized by specific dietary goals and preferences, such as weight loss, muscle gain, or dietary restrictions. Users effortlessly explore and subscribe to meal plans, accompanied by detailed recipes and grocery lists. The platform seamlessly integrates a supplier marketplace within its digital health and fitness module, facilitating automatic meal logging and progress tracking.

12 Claims, 2 Drawing Sheets

DIGITAL PLATFORM, SYSTEM, AND METHOD FOR PROVIDING THIRD-PARTIES/USERS MEAL PLANS PROVIDED BY PROFESSIONAL DIETICIANS VIA A DIGITAL HEALTH AND FITNESS PLATFORM

FIELD OF THE INVENTION

The present invention relates generally to health and wellness management, personalized meal, and meal planning, and more particularly, to a digital platform, system, and method for providing third-parties/users meal plans provided by professional dieticians via a digital health and fitness platform.

BACKGROUND OF THE INVENTION

As a result of changes in socioeconomic conditions, a growing number of individuals in both developed and developing countries are grappling with issues related to overweight and obesity. This trend is largely attributed to a sedentary lifestyle and unhealthy eating habits. Notably, statistics reveal a significant increase in obesity rates, particularly in developed nations like the United States, since the 1980s, and this percentage continues to rise steadily.

It is essential to recognize that overweight and obesity are closely linked to a heightened risk of non-communicable diseases, including type 2 diabetes, hypertension, stroke, asthma, arthritis, and a general decline in health status. Such health issues can significantly diminish individuals' quality of life due to suboptimal dietary choices. Consequently, this has become a pressing public health concern that has garnered significant attention globally.

However, it is crucial to acknowledge that despite the changing socioeconomic landscape, a lack of awareness regarding nutrition and healthy lifestyle practices is contributing to an increased risk of overweight, obesity, and unhealthy eating patterns. Therefore, there is a compelling need to establish preventive strategies aimed at promoting awareness of balanced diets and active lifestyles. This can ultimately lead to improved overall population health, enhanced fitness levels, and better dietary practices. The key to achieving these goals lies in the widespread availability of healthcare services and platforms.

To address these challenges effectively, healthcare services and platforms must leverage information and communication technology to make nutritional information more accessible, efficient, and impactful. Such systems can provide vital support to individuals in their efforts to cultivate healthier daily routines. One innovative approach is the development of third-party meal plans within digital health and fitness platforms. These plans can serve as valuable guides for making informed decisions about nutrition and meal planning, thus contributing to better overall health and well-being.

Various supportive tools, such as web-based meal planning systems, food recommender systems, and knowledge-based dietary nutrition recommendations, have emerged as valuable aids in managing meal plans. These tools offer considerable assistance; however, users often encounter limitations when it comes to accessing a diverse range of meal plans that align with their specific dietary requirements and preferences. Furthermore, these tools typically fall short of delivering personalized menu plans crafted by professional dietitians or nutritionists.

The challenge lies in the fact that planning a healthy and nutritionally balanced meal can be a daunting task, particularly for individuals who lack the necessary knowledge and practical skills to translate nutritional information into action. Moreover, the process of meal planning can become time-consuming and frustrating, especially for those who attempt it without a comprehensive understanding of nutrition and the appropriate dietary choices. This issue is compounded for individuals who may lack the motivation and readiness to engage in this process.

Notably, in industrialized countries, there has been a significant shift in eating habits and cooking practices. These changes in dietary behaviors and food preparation methods have further underscored the need for effective meal planning and nutrition guidance to address the evolving demands of modern lifestyles.

To begin, there has been a decline in the amount of time people spend on cooking. In the United States, this reduction is notable, as it has decreased from 1 hour and 63 minutes per day in 1965-1966 to 58 minutes in 2006-2007. Furthermore, the sources of the food people consume have undergone significant changes. There is a decrease in the consumption of homemade meals prepared with fresh ingredients and essential food nutrients, while the consumption of meals prepared outside the home has become a more substantial part of people's diets.

Given these observations, numerous studies have examined the potential impact of effective meal planning on various aspects, including dietary quality, health-related issues like allergies, and weight status. These studies have consistently found that consuming food without consideration of these factors is linked to a lower quality diet and a higher body mass index, which in turn can lead to health risks. In contrast, properly planned meals that incorporate all necessary nutrients have shown several benefits, including improved adherence to dietary goals, and higher consumption of fruits, vegetables, fiber, folate, and vitamins. Consequently, meal planning is increasingly promoted as a strategy to enhance dietary quality and discourage unhealthy eating habits.

Traditionally, crafting personalized meal plans has been a laborious and time-consuming endeavor, involving individual research, grocery shopping, meal preparation, and meticulous portion control-all aimed at aligning with specific dietary and nutritional requirements. Moreover, the existing meal planning services, although convenient, often fall short of accommodating precise dietary needs and personal preferences. These services typically lack the involvement of professionals like dietitians and tend to offer fixed menus, limiting flexibility for personalization or adjustments based on changing nutritional goals and preferences.

Hence, there arises a clear need for a comprehensive system and method to offer third-party meal plans within a digital health and fitness platform. This integrated digital platform is meticulously designed to empower users in their pursuit of health, fitness, and dietary objectives through tailor-made meal plans, fitness monitoring, and related services. It stands out by presenting third-party meal plans crafted by certified dietitians and nutritionists. This unique feature establishes a platform for nutrition experts to share their knowledge and meal plans with platform users. These third-party meal plans are thoughtfully categorized, catering to specific dietary objectives or preferences, such as weight management, muscle building, veganism, vegetarianism, gluten-free and dairy-free options, among others.

US Patent Application No. US20100136508A1 discloses a meal plan is generated based on user health data, goals and other information. The data regarding user health goals, eating habits, current health condition, and eating preferences is accessed. A user meal plan is then generated based on at least a portion of the accessed information. The meal plan may be modified based on user selected substitutions, automatically generated substitutions, or in some other manner. When the meal plan is modified, information related to the meal plan is updated.

US Patent Application No. US20080086374A1 discloses computerized systems and methods for nutritional planning are disclosed that may comprise providing a database coupled to a central terminal, storing in the database a plurality of records comprising nutritional information related to products available for purchase using a loyalty profile, and associating in the database the nutritional information with products purchased using the loyalty profile. These systems and methods may further comprise identifying deficiencies in a nutritional profile and displaying products which compensate for deficiencies.

US. Patent Application US20040210456A1 discloses a weight control software system and method may provide an interactive software environment to a user via a network to enhance the ability of users to follow a weight control program. The weight control software system may generate meal plans that are automatically updated based on an updated weight of the user following the weight control program. A variety of tools may be integrated into the weight control software system and be interoperable to utilize information entered by the user or generated by the system in controlling body weight of the user. Such tools may include varying meal plan types and varying schemes for generating meal plans.

US. Patent Application US20210104173A1 discloses a System and methods for a comprehensive and personalized approach to health and lifestyle coaching are described. The system may determine health metrics of a user based on detected physiological parameters. The health metrics may be used to determine health recommendations and transmit feedback to the user based on user compliance with the recommendations.

US20190295440A1 provide methods and systems for providing personalized food and health management recommendations. The method may comprise mapping foods by abstracting information from data relating to foods to develop a food ontology. The method may comprise collecting and aggregating a plurality of data sets related to food, health, or nutritional information of a user. The plurality of data sets may be provided from a plurality of sources in a two or more data formats. The method may comprise converting the plurality of data sets into a standardized format that may be individualized for the user. The method may comprise applying a predictive model to the food ontology and the plurality of data sets of the user in the standardized format to determine effects of food consumption of the user's body.

The existing systems and platforms for meal planning and dietary management exhibit several limitations that need to be addressed. Traditional personalized meal planning is a time-consuming process that places a heavy burden on individuals, requiring extensive research, shopping, preparation, and portion control. Even when convenient meal planning services are available, they often lack the flexibility to cater to specific dietary requirements and personal preferences. These services typically do not involve professionals such as dietitians, and they offer fixed menus that leave little room for adaptation as nutritional needs and preferences evolve.

To overcome these challenges and improve the landscape of meal planning and dietary management, there is a clear need for an integrated digital health and fitness platform. Such a platform should provide customizable meal plans created by registered dietitians and nutritionists, offering expertise and personalized guidance to users. These third-party meal plans should be categorized according to various dietary goals and preferences, ensuring that individuals can access plans tailored to their specific needs, whether it's for weight management, muscle building, or adherence to specific diets like vegan, vegetarian, gluten-free, or dairy-free.

Moreover, the digital platform should seamlessly integrate fitness tracking, nutritional information, and other related services to provide users with a holistic approach to health and wellness. By bridging the gap between professional expertise and user convenience, this platform can empower individuals to make informed dietary choices, improve their overall health and fitness, and ultimately lead healthier, more fulfilling lives. In doing so, it can address the limitations of existing systems and offer a comprehensive solution to the challenges of meal planning and dietary management in the modern world.

SUMMARY OF THE INVENTION

To address the foregoing problems, in whole or in part, and/or other problems that may have been observed by persons skilled in the art, the present disclosure provides compositions and methods as described by way of example as set forth below.

A principal object of the invention is to provide an integrated digital health and fitness platform that simplifies and enhances personalized meal planning, making it more accessible, efficient, and effective for users.

Another object of the invention is to provide users with a wide variety of customizable meal plans created by certified dietitians and nutritionists, addressing specific dietary goals and preferences such as weight management, muscle building, and various dietary restrictions.

Another object of the invention is to bridge the gap between professional expertise and user convenience by offering comprehensive meal plans that not only include recipes but also detailed nutritional information, grocery lists, and step-by-step instructions, thereby promoting healthier dietary choices.

Another object of the invention is to foster collaboration between nutrition professionals, users, and suppliers, creating a win-win scenario by expanding the reach of dietitians, generating additional income for professionals, and driving platform revenue growth while improving the overall health and wellness of the user community.

In a first implementation of the invention, there is provided a system designed to deliver personalized meal plans to users via a digital health and fitness platform, comprising a set of integral components. These components include a user interface adept at gathering personal data encompassing body metrics, fitness objectives, dietary preferences, and allergies. An advanced algorithm is employed to compute individual dietary requirements, factoring in Basal Metabolic Rate (BMR), Resting Metabolic Rate (RMR), and Total Daily Energy Expenditure (TDEE) based on the collected personal data. Furthermore, a dedicated data store caters to meal planners, including registered dietitians and nutritionists, offering them the ability to upload meal offerings and nutritional information. A sophisticated matching algorithm then comes into play, comparing user-specific dietary requirements with available meals in the data store, thereby filtering and presenting options that precisely align with the user's nutritional needs. To facilitate user convenience, an order placement module is incorporated, enabling users to effortlessly place orders for selected meals within the platform. Additionally, a notification module is utilized to promptly alert meal providers about placed orders, ensuring efficient order fulfillment and a seamless user experience.

In a second aspect of the invention, the meal plans can be categorized based on specific dietary goals or preferences, including weight loss, muscle gain, vegan, vegetarian, gluten-free, dairy-free, or other dietary preferences.

In another aspect of the invention, the system may further comprise a digital health and a fitness module that integrates a supplier marketplace with subscribed meal planners and automatically logs meals from subscribed plans into user daily meal logs, allowing users to track their dietary intake and progress toward health goals seamlessly.

In another aspect of the invention, the system may further comprise a Meal Database Engine (MDE) that uses cost-based tagging, macronutrient analysis, cuisine classification, dietary preference filtering, ingredient-based categorization, meal data expansion, user feedback integration, and personalized meal recommendations to enhance the user experience.

In another aspect of the invention, the system may comprise a meal planner engine that collects user data, calculates metrics like BMI, BMR, and RMR, and generates meal plans based on user dietary preferences and goals.

In another aspect of the invention, the system may comprise a supplier queue engine that manages supplier queues for meal delivery, supporting targeted and efficient supplier interactions within the platform.

In a second implementation of the invention, there is provided a method for providing personalized meal plans to users via a digital health and fitness platform. The method comprises the steps of collecting personal data from users, including body metrics, fitness goals, dietary preferences, and allergies, through a user interface, calculating individual dietary requirements for each user based on the collected personal data, incorporating Basal Metabolic Rate (BMR), Resting Metabolic Rate (RMR), and Total Daily Energy Expenditure (TDEE) through an algorithm, maintaining a data store containing meal offerings and nutritional information from registered dietitians and nutritionists, which can be uploaded to the data store, employing a matching algorithm to compare the dietary requirements of each user with available meals in the data store, thereby filtering meal options that align with each user's specific dietary needs, allowing users to place orders for selected meals within the platform through an order placement module and utilizing a notification module to inform meal providers of the orders placed by users for fulfillment.

In an another implementation of the invention, there is provided a digital platform for health and wellness management. The digital platform comprises a user interface configured to collect personal data from users, including body metrics, fitness goals, dietary preferences, and allergies, an algorithm for calculating individual dietary requirements for each user based on the collected personal data, incorporating Basal Metabolic Rate (BMR), Resting Metabolic Rate (RMR), and Total Daily Energy Expenditure (TDEE), a data store containing meal offerings and nutritional information from registered dietitians and nutritionists, allowing for the uploading of meal plans and related data, a matching algorithm that compares user dietary requirements with available meal options in the data store, filtering meal choices to align with individual user dietary needs, an order placement module facilitating users to place orders for selected meals within the platform; and a notification module for informing meal providers of placed orders, ensuring efficient order fulfillment.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The subject matter of the present invention now will be described more fully hereinafter with reference to the accompanying drawings, in which some, but not all embodiments of the subject matter of the present invention are shown. Like numbers refer to like elements throughout. The subject matter of the present invention may be embodied in many different forms and should not be construed as limited to the embodiments set forth herein; rather, these embodiments are provided so that this disclosure will satisfy applicable legal requirements. Indeed, many modifications and other embodiments of the subject matter of the present invention set forth herein will come to mind to one skilled in the art to which the subject matter of the present invention pertains having the benefit of the teachings presented in the foregoing descriptions and the associated drawings. All illustrations of the drawings are for the purpose of describing selected versions of the present invention and are not intended to limit the scope of the present invention. Therefore, it is to be understood that the subject matter of the present invention is not to be limited to the specific embodiments disclosed and that modifications and other embodiments are intended to be included within the scope of the appended claims.

Shown throughout the figures, the present invention is directed to a system, method, and digital platform that are transforming the landscape of health and wellness management through individualized meal planning and fitness monitoring. This user-centered system efficiently gathers crucial personal information, including body measurements, fitness objectives, dietary choices, and allergies, through an intuitive interface. Employing advanced algorithms, which encompass Basal Metabolic Rate (BMR), Resting Metabolic Rate (RMR), and Total Daily Energy Expenditure (TDEE), the platform precisely computes custom dietary needs for each user. A robust data repository empowers registered dietitians, nutritionists, and experts to upload an array of meal options, categorized according to specific dietary goals and preferences, such as weight management, muscle building, or dietary restrictions. Users can easily explore and subscribe to tailored meal plans, complete with comprehensive recipes and shopping lists. Furthermore, the platform seamlessly integrates a supplier marketplace within its digital health and fitness module, streamlining meal tracking and progress monitoring automatically.

The system for providing third-party meal plans on a digital health and fitness platform requires customers to log into the platform and app of the disclosed invention via the Internet. Furthermore, customers/users provide various details including but not limited to their body metrics (weight, height, age), activity levels, fitness goals, dietary preferences, and allergies the platform then creates a customer profile datastore with Unique ID, from the personal details of the user which further comprises of information such as names, contact info, activity metrics, burnt calories, consumed calories, macro needs, calorie needs, metabolism data, physical metrics, health metrics such as; BMI and BMR, dietary preferences and restrictions, nutritional goals, meal preferences, order history, securely-stored payment information, and delivery address. These variables are integral to calculating individual dietary and nutritional requirements. The invention algorithms calculate the customer's daily calorie and macronutrient (protein, carbohydrates, and fat) needs. The calculations account for the user's Basal Metabolic Rate (BMR), Resting Metabolic Rate (RMR), and Total Daily Energy Expenditure (TDEE). These metrics are crucial in customizing an individual's dietary needs according to their fitness goals such as weight loss, muscle gain, or maintenance. The system further uses a personalization algorithm to calculate customer nutritional needs and generate meal recommendations and filters the algorithm based on customer allergies, and preferences. Once done, the customer is provided with options to place an order from existing meals or subscribe to meal plans from the meal planner marketplace platform for meals matching their various and specific needs across various cuisines that suit the user/customer preference.

In an embodiment, the disclosed meal planners platform introduces a streamlined process for dietitians and nutritionists to access the platform and application of the current invention. They are required to furnish a range of information, including but not limited to their brand details, pertinent health licenses and credentials, comprehensive meal-related data encompassing cuisine, dietary specifications, and allergy considerations, as well as their meal plan objectives, accompanied by relevant images and pricing details. This wealth of information is systematically cataloged within the data store dedicated to meal planners and subsequently made available on the meal marketplace.

Subsequently, customers engage with the meal marketplace through the platform of the present invention, where they are presented with a diverse array of meal plans meticulously tailored to align with their individual dietary goals, fitness aspirations, allergies, and other essential particulars. Customers are then empowered to select and subscribe to a specific meal plan, which not only includes a collection of recipes but also comprehensive meal preparation instructions. Additionally, the disclosed supplier network flow chart is a valuable component of this innovation, providing further insights into the intricate workings of the platform. This inventive process enhances the accessibility of expertly crafted meal plans while fostering seamless interactions between customers, dietitians, nutritionists, and meal providers.

In an embodiment, the disclosed invention introduces a comprehensive system and method that establishes a data repository tailored to meal suppliers. This repository functions as a centralized hub where suppliers can effortlessly input their meal offerings, accompanied by thorough nutritional details. The invention goes a step further by implementing artificial intelligence-based systems or manual interventions to refine and cleanse the data. Suppliers are tasked with entering a wide array of information, including brand specifics, vendor availability, cuisine categories, payment particulars, vendor identity, and description, meal particulars like name/ID and description, meal macros, nutritional facts, allergy considerations, ingredients, dietary classifications (such as Keto or Vegan), tags like "high protein" or "pre-workout," images, costs, preparation times, cooking instructions, meal shelf life, and other requisite information. Once entered, this data is stored within the supplier's profile and is subjected to further enhancement through AI-driven refinement or manual proofreading.

The refined data is then preserved for algorithmic purposes and is instrumental during the filtering and matching processes, becoming accessible to customers when they engage with the supplier marketplace platform of the present invention. When a customer places an order through the platform, suppliers are promptly alerted and can accept the orders and update meal-related data as needed. Subsequently, the supplier proceeds with meal preparation and order fulfillment. Importantly, the platform of this invention seamlessly integrates meal data from subscribed plans into the user's daily meal log, automating the tracking of dietary intake and progress toward health goals. This integration ensures a user-friendly experience, empowering individuals to easily monitor their dietary choices and measure their journey toward improved health.

In an embodiment, at the forefront of this system is a user interface that serves as the point of interaction between users and the platform. This interface empowers users to provide essential personal data, including body metrics, fitness aspirations, dietary preferences, and allergies. These inputs serve as the foundation upon which the entire personalized wellness journey is built. It is worth noting that the meal plans available within the platform are meticulously crafted by registered dietitians and nutritionists. These professionals bring their expertise to the table, ensuring that the meal offerings are not only diverse but also tailored to specific dietary goals or preferences. This level of personalization, spanning categories such as weight loss, muscle gain, veganism, vegetarianism, gluten-free, and dairy-free diets, sets the platform apart from conventional solutions.

Beneath the surface of the system lies a powerful algorithm designed to calculate individual dietary requirements with precision. Leveraging key metrics like Basal Metabolic Rate (BMR), Resting Metabolic Rate (RMR), and Total Daily Energy Expenditure (TDEE), this algorithm creates a personalized roadmap for users to achieve their nutritional objectives. This level of dietary sophistication is a novel addition to the landscape of health and fitness platforms.

In an embodiment, the system also includes a centralized data store, where registered dietitians, nutritionists, and other meal planners can upload their offerings and nutritional information. This repository ensures that users have access to a rich and diverse selection of meal plans. It serves as the backbone of the platform, enabling users to explore a wide range of meal options aligned with their dietary needs and preferences.

In an embodiment, a cornerstone of this system is the intelligent matching algorithm. This algorithm serves as the catalyst that aligns user dietary requirements with the wealth of meal options stored in the data store. It operates with precision, filtering and curating meal options that seamlessly align with the user's specific dietary needs. This dynamic matching process ensures that users are presented with meal choices that are not only suitable but also appealing.

In an embodiment, the system goes a step further by allowing users to place orders for their selected meals directly within the platform. An integrated notification module informs meal providers of these orders, facilitating efficient fulfillment. Users have the flexibility to browse various meal plans and subscribe to those that resonate with their dietary needs and preferences. The provided meal plans come complete with comprehensive details, including recipes, grocery lists, and step-by-step instructions, enhancing user convenience and promoting adherence to dietary goals.

In an embodiment, the system seamlessly integrates a digital health and fitness module, elevating the user experience to new heights. The module functions as a supplier marketplace, where meal planners can connect with users and automatically log meals from subscribed plans into users' daily meal logs. This integration empowers users to effortlessly track their dietary intake and monitor their progress toward their health goals.

In an embodiment, beyond the individual user experience, the digital health and fitness module fosters a win-win ecosystem. It not only benefits users by offering personalized meal plans but also empowers meal planners and suppliers. Nutrition professionals can expand their reach, generate additional income, and contribute to platform revenue growth.

In an embodiment, central to the system is the Meal Database Engine (MDE), a powerhouse that enhances the user experience. This engine employs an array of tools, including cost-based tagging, macronutrient analysis, cuisine classification, dietary preference filtering, ingredient-based categorization, meal data expansion, user feedback integration, and personalized meal recommendations. These tools collectively elevate the user experience, providing tailored meal suggestions that align precisely with user preferences and goals.

In an embodiment, the system is further fortified by the Meal Planner Engine, which streamlines the meal planning process. This engine collects user data, including metrics like Body Mass Index (BMI), BMR, and RMR, to generate meal plans that are personalized to each user's dietary preferences and objectives. Further, there is provided a supplier queue engine is an integral component that manages supplier queues for meal delivery. It ensures that supplier interactions within the platform are targeted and efficient, streamlining the meal delivery process.

Recognizing the diverse needs of users, the system seamlessly integrates with third-party health and fitness apps. This integration tailors the solution to users seeking personalized meal plans while also offering suppliers a channel to reach a specific customer base.

Figure 1:
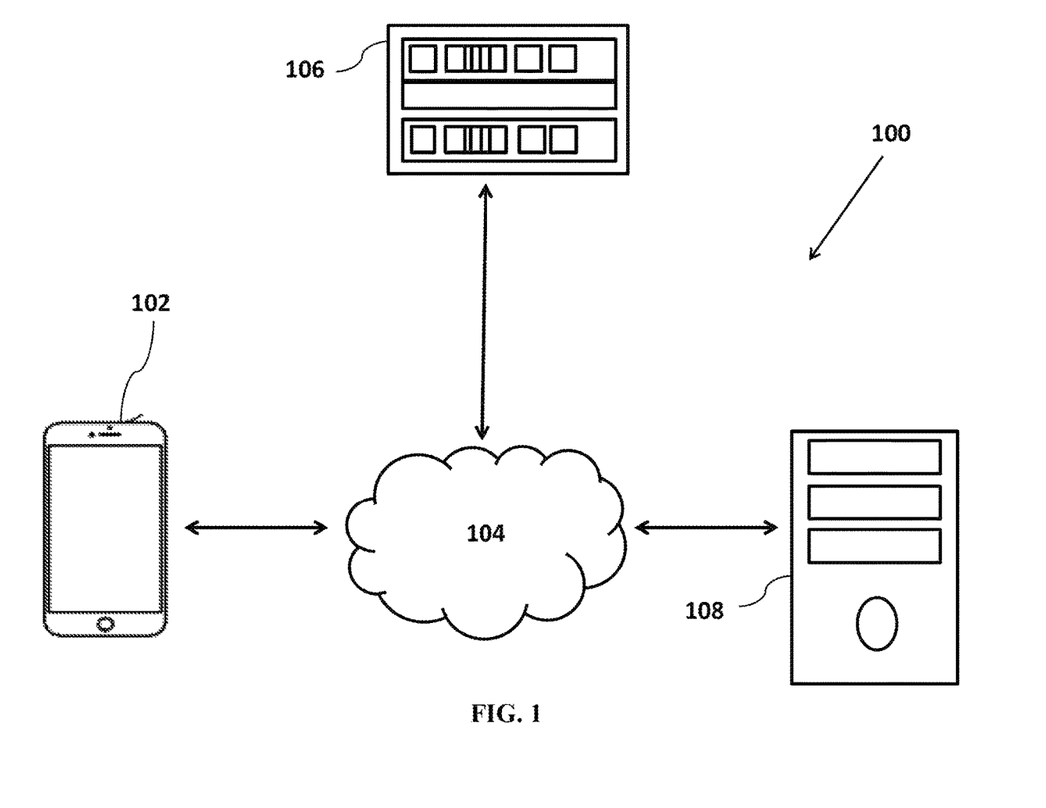
FIG. 1 illustrates a block diagram of the system for providing personalized meal plans to users via a digital health and fitness platform, in accordance with an embodiment of the present invention.

In accordance with an embodiment of the present invention, FIG. 1 illustrates a block diagram of the system for providing personalized meal plans to users via a digital health and fitness platform. The user interface 102 serves as the entry point for users to interact with the platform. In an example, the user interface could be a smartphone, tablet, laptop, etc. Users access the system through this interface 102, providing crucial personal data that includes body metrics, fitness goals, dietary preferences, and allergies. This data forms the foundation for the system's personalized meal-planning capabilities. Further, there is provided an internet connection 104 which is vital for the system's operation, as it enables the seamless transmission of data between the user interface and various backend modules. This connection ensures real-time data processing and access to a wide range of resources, including the database.

Further, the algorithm-based calculation and comparison module 106 plays a pivotal role. It employs sophisticated algorithms to process the personal data collected via the user interface. This module calculates individual dietary requirements using key metrics such as Basal Metabolic Rate (BMR), Resting Metabolic Rate (RMR), and Total Daily Energy Expenditure (TDEE). Furthermore, it carries out a dynamic comparison of these calculated requirements with the extensive meal offerings stored in the database 108.

The database 108 as shown in FIG. 1 serves as a centralized repository for meal planners, including registered dietitians and nutritionists. These professionals upload a wealth of valuable meal information, encompassing nutritional details, ingredient lists, dietary classifications, and much more. The database is the treasure trove of meal-related data that the system taps into when generating personalized meal plans. It houses the diverse meal options available to users, categorized based on specific dietary goals or preferences.

Figure 2:
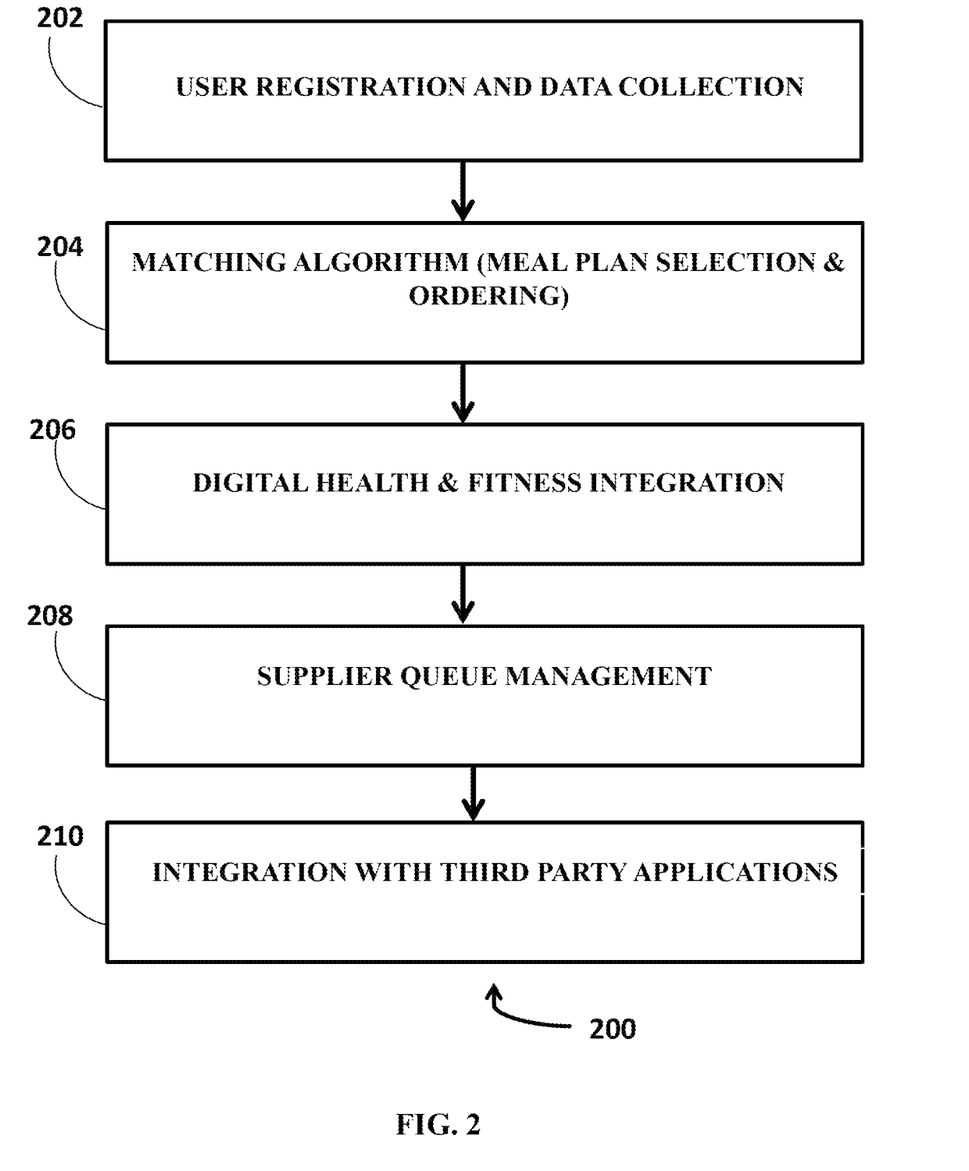
FIG. 2 illustrates a method flow diagram of the method for providing personalized meal plans to users via a digital health and fitness platform, in accordance with an embodiment of the present invention.

In accordance with an embodiment of the present invention, FIG. 2 shows a method flow diagram of the method 200 for providing personalized meal plans to users via a digital health and fitness platform. Users begin by registering 202 on the digital health and fitness platform, where they provide essential personal data including body metrics, fitness goals, dietary preferences, and allergies through the user interface. Subsequently, an algorithm processes this collected data, calculating individual dietary requirements by considering factors such as Basal Metabolic Rate (BMR), Resting Metabolic Rate (RMR), and Total Daily Energy Expenditure (TDEE). Registered dietitians and nutritionists play a significant role as they upload detailed meal offerings and nutritional information into the data store. A sophisticated matching algorithm 204 then comes into play, comparing user dietary requirements with the extensive meal database. It efficiently filters out meal options that precisely align with the user's needs, preferences, and restrictions. Users, having personalized meal options at their disposal, proceed to browse, select, and place orders for the meals that best suit their dietary requirements and preferences. A notification module informs meal providers of these placed orders, initiating the meal preparation and fulfillment process to ensure users receive their selected meals promptly. Users gain access to their chosen meal plans, which include comprehensive details such as recipes, grocery lists, and step-by-step instructions for meal preparation.

Further, as shown in FIG. 2, the digital health and fitness module integrates 206 seamlessly with the supplier marketplace and meal planners, allowing for the automatic logging of meals from subscribed plans into user daily meal logs. This integration enables users to track their dietary intake and monitor their progress toward their health and fitness goals. Moreover, a Meal Database Engine (MDE) enriches the user experience by providing tailored meal recommendations, cost-based tagging, macronutrient analysis, and more, all of which contribute to a personalized approach to meal planning. Additionally, a Meal Planner Engine collects and processes user data, utilizing metrics like BMI, BMR, and RMR to generate meal plans that align with user dietary preferences and objectives.

Further, to ensure efficient interactions within the platform, a Supplier Queue Engine manages supplier queue 208 for meal delivery, optimizing the meal fulfillment process.

Finally, the system maintains its flexibility and convenience by integrating 210 with third-party health and fitness apps, expanding its functionality and catering to a broader user base seeking personalized meal plans.

The essence of the disclosed invention revolves around its innovative approach, which harmoniously connects meal preparation suppliers with customers through an intelligent and highly personalized meal planning system. What sets this platform apart is its exceptional capability to collect comprehensive meal-related data from suppliers, analyze this information in the context of each customer's dietary preferences and nutritional objectives, and ultimately create a tailored meal plan that precisely corresponds to these preferences and goals. This distinctive fusion of data-driven personalization, dietary science, and seamless supplier-customer interaction represents a groundbreaking advancement in the realm of meal planning and delivery.

At the core of the invention is the convergence of technology and nutrition expertise. By allowing meal suppliers to input detailed information about their offerings, including meal components, nutritional content, dietary classifications, and more, the platform establishes a robust database of meal options. The incorporation of artificial intelligence and manual proofreading ensures that this data is not only accurate but also constantly refined and updated.

On the customer side, individuals provide vital information regarding their dietary preferences, restrictions, and health objectives. The magic of this invention lies in its ability to bridge these two sets of information-supplier data and customer preferences. The platform employs a sophisticated algorithmic approach to match and filter meal options from suppliers in a way that seamlessly aligns with each user's specific dietary needs and goals. This personalized meal planning process goes beyond mere convenience; it empowers users to make informed and healthier dietary choices.

In an embodiment, the heart of the disclosed invention lies in the development and application of a highly advanced matching algorithm, which sets it apart from conventional meal-planning systems. This algorithm serves as the brain behind the platform, performing a multifaceted role that extends beyond mere meal filtering and matching. Its sophistication lies in its ability to go several steps further, ensuring that the aggregated nutritional content of the proposed daily or weekly meal plans aligns impeccably with each user's unique nutritional objectives.

At its core, this algorithm is dynamic and operates in real-time, a crucial aspect that allows it to adapt and evolve continuously. This real-time processing and matching system takes into account several dynamic factors, including user feedback, updates from meal suppliers, and advancements in dietary science. This adaptability and responsiveness ensure that the meal plans generated are not static but rather remain tailored to the ever-evolving needs and preferences of each user.

The algorithm's primary role is to analyze an extensive array of meal options provided by suppliers, factoring in a multitude of variables, including dietary preferences, restrictions, and nutritional objectives specified by the user. It meticulously cross-references this supplier data with user profiles to generate meal plans that not only align with personal dietary preferences but also ensure that the cumulative nutritional content harmonizes with the user's specific nutritional goals. This level of precision and personalization goes beyond traditional meal planning systems, which often overlook the importance of nutritional balance.

Furthermore, the algorithm's adaptability is a game-changer. It doesn't rely solely on initial user inputs; instead, it learns and refines its recommendations over time. User feedback helps it fine-tune meal suggestions, while it can promptly incorporate updates from meal suppliers, ensuring that users are exposed to the most current and appealing meal options. Moreover, as dietary science evolves and our understanding of nutrition deepens, the algorithm remains flexible, adjusting its recommendations to incorporate the latest insights and guidelines.

In an embodiment, the core algorithm that drives this innovation operates through a well-defined sequence of steps, each contributing to the creation of truly personalized and nutritionally balanced meal plans. These steps collectively represent a pioneering approach that sets this platform apart from industry norms.

Data Collection: The process begins with the collection of comprehensive meal-related data from meal suppliers, covering various aspects of each meal they offer. Concurrently, detailed dietary preferences and nutritional objectives are gathered from users. This marks the foundation of the personalized meal planning process.

Initial Filtering: The algorithm then embarks on the initial filtering stage, where it judiciously sifts through the vast array of meals available. It efficiently eliminates meals that do not align with the user's dietary restrictions and preferences. This step is pivotal in ensuring that the meal options considered for the user are already a closer match to their individual needs and preferences.

Nutritional Matching: A pivotal and distinctive phase in the algorithm's operation is the nutritional matching step. Here, the algorithm takes on the task of amalgamating the nutritional content of various meals to construct a meal plan that meticulously aligns with the user's daily nutritional objectives. It leverages a deep understanding of nutritional science to ensure that not only are the user's dietary preferences met, but their nutritional goals are also addressed.

Plan Generation: The final phase of the algorithm's operation involves the generation of a comprehensive meal plan. This plan is meticulously crafted to meet the user's specified nutritional goals while also offering variety and adhering to their dietary preferences. It ensures that users receive a holistic meal plan that is not only aligned with their dietary and nutritional needs but is also enjoyable and diverse.

What truly set this algorithm apart is the seamless integration of supplier meal data with user dietary preferences and the principles of nutritional science. This approach ensures that the resulting meal plans are not only personalized but also nutritionally sound and balanced. It's worth noting that this type of integrated algorithm is a pioneering concept within the industry, where meal planning has traditionally been less precise and personalized.

In an embodiment, the matching algorithm at the core of this innovation has been meticulously designed to serve as a powerful tool that seamlessly aligns user dietary requirements with the wealth of nutritional information stored in the data store. This algorithm operates in a structured and tiered manner, with each step aimed at refining and optimizing the meal planning process to ensure the best possible user experience.

Initial Comparison: The first tier of the algorithm's operation is dedicated to an initial comparison process. In this phase, the algorithm efficiently filters out meals from the data store based on various user-specific criteria. It takes into account dietary restrictions, such as allergens, as well as dietary preferences, such as vegan or keto diets, and other tagged attributes that users have specified. This initial filtration step helps ensure that only meals that are compatible with the user's dietary limitations and preferences are considered for further evaluation.

Nutritional Matching: Moving to the second tier, the algorithm engages in a comprehensive nutritional matching process. Here, it goes beyond basic compatibility and delves into the nutritional content of the remaining meal options. It scrutinizes these meals against the user's specific dietary goals, with the overarching objective of identifying a combination of meals that collectively meet the user's daily or weekly nutritional targets. This phase is pivotal in ensuring that the meal plan generated not only aligns with the user's dietary preferences but also contributes to their broader nutritional objectives.

Optimization: The algorithm doesn't stop at the basic matching of meals; it also incorporates an optimization step. This optimization process is geared towards providing users with a diverse array of meal options while still staying within the bounds of their nutritional goals. It aims to create a balanced and enjoyable meal plan that not only meets the user's dietary needs but also offers variety, enhancing the overall dining experience.

One of the hallmark features of this algorithm is its real-time adaptability. It is designed to be dynamic and responsive, capable of adjusting to changing circumstances. This includes changes in meal availability, shifts in user preferences, and feedback received from users. This adaptability ensures that users receive meal plans that are not only precisely tailored to their immediate needs but can also evolve over time to reflect their changing dietary preferences and objectives.

The matching algorithm represents a pivotal element of this invention, orchestrating a highly sophisticated and personalized meal-planning process. Its tiered approach, encompassing initial comparison, nutritional matching, and optimization, ensures that users receive meal plans that are both nutritionally sound and enjoyable. Moreover, its real-time adaptability ensures that the meal planning experience remains responsive to the ever-changing dynamics of user preferences and meal availability, cementing its position as a key feature of this groundbreaking invention.

In an embodiment, the supplier engine stands at the forefront of the disclosed system and platform, serving as the critical bridge connecting meal preparation suppliers with the comprehensive ecosystem. Its operation encompasses a series of well-defined steps, each contributing to the seamless integration of meal offerings into the platform, all while upholding the highest standards of data accuracy and quality.

Meal Information Upload: The process commences with meal suppliers utilizing a dedicated portal to upload an exhaustive wealth of information about each meal they offer. This step is pivotal in establishing a robust foundation for the subsequent stages of the operation. Suppliers are empowered to input comprehensive details, encompassing meal components, nutritional content, dietary classifications, pricing, images, and more. This thorough meal information serves as the bedrock of the platform's meal offerings.

Data Validation and Quality Check: Following the upload of meal information, the Supplier Engine assumes the role of guardian, conducting rigorous validation checks on the incoming data. These validation procedures are instrumental in ensuring the accuracy and completeness of the meal-related information. Any discrepancies or inaccuracies are promptly identified and addressed, safeguarding the integrity of the data that feeds into the platform.

Database Storage: The validated meal information is meticulously organized and stored within a structured and indexed database. This storage mechanism is designed for optimal efficiency, enabling rapid and precise querying of meal data. The structured database not only facilitates swift access to meal options but also enhances the overall performance and responsiveness of the platform.

Meal Availability Updates: In recognition of the dynamic nature of meal availability, suppliers are granted the capability to update crucial meal details in real-time. This encompasses adjustments to meal availability, pricing modifications, and any other pertinent updates. These real-time updates are seamlessly integrated into the platform, ensuring that users have access to the most current and accurate meal options.

Feedback Loop: As an added dimension of the Supplier Engine's operation, it provides a valuable feedback loop for meal suppliers. Suppliers receive comprehensive feedback and analytics on the performance of their meal offerings within the platform. This feedback mechanism offers insights into user preferences, meal popularity, and other key metrics. Armed with this invaluable information, suppliers can make informed adjustments to their offerings, ultimately enhancing the quality and appeal of their meals to a broader audience.

The supplier engine embodies a pivotal role within the disclosed system and platform, orchestrating the systematic onboarding of meal options while safeguarding data accuracy and completeness. Through its meticulous operation, which encompasses meal information upload, data validation, structured database storage, real-time updates, and a feedback loop for suppliers, it plays a fundamental part in ensuring that users have access to a diverse and ever-evolving selection of high-quality meals. This, in turn, contributes to an enriched and dynamic user experience, setting the disclosed system and platform apart as a robust and responsive solution in the realm of health and wellness management.

Some of the non-limiting advantages of the present invention are:

- The invention provides tailored meal plans based on users' body metrics, fitness goals, dietary preferences, and allergies, promoting personalized and healthier eating habits.
- Users gain access to a wide array of meal plans crafted by registered dietitians and nutritionists, catering to specific dietary goals and preferences, ensuring expert guidance.
- The platform simplifies meal planning by allowing easy browsing, selection, and ordering of meals with detailed instructions, eliminating the hassle of meal preparation.
- Users can monitor their dietary intake and fitness progress seamlessly, thanks to the integrated digital health and fitness module, enhancing accountability and informed decision-making.
- The system offers a platform for nutrition professionals and suppliers to expand their reach, generate income, and collaborate within the health and wellness ecosystem, benefiting both users and experts.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A system for providing personalized meal plans to users via a digital health and fitness platform, comprising:
    a user interface configured to collect personal data including body metrics, fitness goals, dietary preferences, and allergies;
    an algorithm for calculating individual dietary requirements based on the collected personal data, incorporating Basal Metabolic Rate (BMR), Resting Metabolic Rate (RMR), and Total Daily Energy Expenditure (TDEE);
    a data store for meal planners, including registered dietitians and nutritionists, to upload meal offerings and nutritional information;
    a matching algorithm that compares user dietary requirements with meals in the data store, filtering options that align with the user's needs;
    an artificial intelligence-based system and manual interventions to refine and cleanse the data;
    an order placement module allowing users to place orders for selected meals within the platform; and
    a notification module to inform meal providers of placed orders for fulfillment.

2. The system of claim 1, wherein the meal plans are categorized based on specific dietary goals or preferences, including weight loss, muscle gain, vegan, vegetarian, gluten-free, dairy-free, or other dietary preferences.

3. The system of claim 1, further comprising a digital health and a fitness module that integrates a supplier marketplace with subscribed meal planners and automatically logs meals from subscribed plans into user daily meal logs, allowing users to track their dietary intake and progress toward health goals seamlessly.

4. The system of claim 3, wherein the digital health and fitness module provides personalized meal plans.

5. The system of claim 1, further comprising a Meal Database Engine (MDE) that uses cost-based tagging, macronutrient analysis, cuisine classification, dietary preference filtering, ingredient-based categorization, meal data expansion, user feedback integration, and personalized meal recommendations to enhance the user experience.

6. The system of claim 1, further comprising a meal planner engine that collects user data, calculates metrics BMI, BMR, and RMR, and generates meal plans based on user dietary preferences and goals.

7. The system of claim 1, further comprising a supplier queue engine that manages supplier queues for meal delivery, supporting targeted and efficient supplier interactions within the platform.

8. The system of claim 1, wherein the system integrates with third-party health and fitness applications to provide a tailored solution for users seeking personalized meal plans and suppliers aiming to reach a specific customer base.

9. The system of claim 1, wherein the dietary requirement calculations are further used to dynamically adjust meal plans over time based on the user's changing health and fitness goals.

10. The system of claim 1, wherein users can browse through a variety of meal plans and switch between different meal plans.

11. A method for providing personalized meal plans to users via a digital health and fitness platform, comprising the steps of:
    collecting personal data from users, including body metrics, fitness goals, dietary preferences, and allergies, through a user interface;
    calculating individual dietary requirements for each user based on the collected personal data, incorporating Basal Metabolic Rate (BMR), Resting Metabolic Rate (RMR), and Total Daily Energy Expenditure (TDEE) through an algorithm;
    maintaining a data store containing meal offerings and nutritional information from registered dietitians and nutritionists, which can be uploaded to the data store;
    employing a matching algorithm to compare the dietary requirements of each user with available meals in the data store, thereby filtering meal options that align with each user's specific dietary needs;
    implementing artificial intelligence-based systems or manual interventions to refine and cleanse the data
    allowing users to place orders for selected meals within the platform through an order placement module; and
    utilizing a notification module to inform meal providers of the orders placed by users for fulfillment.

12. A digital platform for health and wellness management, comprising:
    a user interface configured to collect personal data from users, including body metrics, fitness goals, dietary preferences, and allergies;
    an algorithm for calculating individual dietary requirements for each user based on the collected personal data, incorporating Basal Metabolic Rate (BMR), Resting Metabolic Rate (RMR), and Total Daily Energy Expenditure (TDEE);
    a data store containing meal offerings and nutritional information from registered dietitians and nutritionists, allowing for the uploading of meal plans and related data;

a matching algorithm that compares user dietary requirements with available meal options in the data store, filtering meal choices to align with individual user dietary needs;

an artificial intelligence-based system and manual interventions to refine and cleanse the data;

an order placement module facilitating users to place orders for selected meals within the platform; and a notification module for informing meal providers of placed orders, ensuring efficient order fulfillment.

* * * * *

UNITED STATES PATENT AND TRADEMARK OFFICE
CERTIFICATE OF CORRECTION

| | | |
|---|---|---|
| PATENT NO. | : 12,106,843 B1 | Page 1 of 1 |
| APPLICATION NO. | : 18/502020 | |
| DATED | : October 1, 2024 | |
| INVENTOR(S) | : Bolaji Agunbiade et al. | |

It is certified that error appears in the above-identified patent and that said Letters Patent is hereby corrected as shown below:

On the Title Page

Under item (12), "Agunbiade" should read -- Agunbiade et al. --.

Item (72), should read as follows:
Bolaji Agunbiade
Adebayo-Ige Toyosi
Blessing Bamiduro
Onikepo Omotade
Tijesunimi Oyetunji
Idris Ganiyu
Kudzi Murefu
Faith Oladejo
Emmanuel Abu
Femi Akinde
David Fawzy
Krish Patel
Damilola Najeem Each of the above inventors resides in Vaughan, Ontario, Canada.

Signed and Sealed this
Twenty-ninth Day of July, 2025

Coke Morgan Stewart
*Acting Director of the United States Patent and Trademark Office*